(12) United States Patent
Karlsson

(10) Patent No.: US 8,230,858 B2
(45) Date of Patent: Jul. 31, 2012

(54) CONTROLLING THE OPERATION OF A RESPIRATORY GAS MONITOR

(75) Inventor: Kai Karlsson, Helsinki (FI)

(73) Assignee: General Electric Company, Schenectady, NY (US)

( * ) Notice: Subject to any disclaimer, the term of this patent is extended or adjusted under 35 U.S.C. 154(b) by 1105 days.

(21) Appl. No.: 12/060,808

(22) Filed: Apr. 1, 2008

(65) Prior Publication Data

US 2009/0241954 A1    Oct. 1, 2009

(51) Int. Cl.
*F16K 31/02* (2006.01)
*A62B 7/00* (2006.01)
(52) U.S. Cl. .......... 128/204.23; 128/204.21; 128/204.18
(58) Field of Classification Search ............. 128/200.24, 128/204.28, 204.21–204.23, 204.26, 205.23; 600/532, 538, 485
See application file for complete search history.

(56) References Cited

U.S. PATENT DOCUMENTS

| | | | |
|---|---|---|---|
| 3,741,208 A * | 6/1973 | Jonsson et al. | 128/204.21 |
| 4,550,726 A | 11/1985 | McEwen | |
| 4,958,075 A | 9/1990 | Mace | |
| 5,873,361 A | 2/1999 | Hakala | |
| 2009/0020122 A1 * | 1/2009 | Hoffrichter | 128/204.23 |

FOREIGN PATENT DOCUMENTS

GB           829 409 A     3/1960

* cited by examiner

*Primary Examiner* — Justine Yu
*Assistant Examiner* — Rachel Young
(74) *Attorney, Agent, or Firm* — Global Patent Operation; Jonathan E. Thomas

(57) ABSTRACT

A method for controlling a respiratory gas monitor device, which includes at least one respiratory gas analyzer, a gas sampling line, a gas pump for sucking sample(s) of respiratory gas from the gas sampling line. Also included are a power supply and a processing unit, and a pressure sensor connected to the gas sampling line and electrically connected to the processing unit. A minimum value and a maximum value in a signal from the patient are detected by the processing unit, and a difference between the minimum value and the maximum value is calculated. The value of this difference is compared with a predetermined threshold value. If the calculated difference is below the threshold value, the pump is switched off or kept non-operating by the processing unit. If the calculated difference is over the threshold value, the pump is switched on or kept operating by the processing unit.

19 Claims, 3 Drawing Sheets

CONTROLLING THE OPERATION OF A RESPIRATORY GAS MONITOR

FIELD OF THE INVENTION

The invention relates a method for controlling the operation of a respiratory gas monitor, which comprises at least one respiratory gas analyzer, a gas sampling line connected to a breathing tube that feeds respiratory gas to and from a patient, a gas pump for sucking a sample flow of respiratory gas from said breathing tube through said gas sampling line, a power supply and a processing unit, and either a pressure sensor connected to said gas sampling line and generating an electrical signal connected to said processing unit, or at least one other patient monitor device capable to detect values of at least one physiological signal from said patient, said other patient monitor detection-connected to said patient and electrical-signal-connected to said processing unit.

BACKGROUND OF THE INVENTION

Respiratory Gas Monitors (=RGM) of the diverting type have a gas pump for drawing a flow of sample gas from the airway of the patient to the RGM. The sample gas is conducted from the sampling site to the RGM by a line with typically 2-3 meters length and internal diameter of about 1.2 mm. The mechanical motion needed for the pumping action is generated using an electrical motor or a solenoid mechanism in the pump. Gas pumps also contain valves actuated by pressure differences within the pump. Regardless of the type of the actuator and the valves, moving mechanical parts in the pump are subjected to stresses and wear, which limit the operating life of the pump. The relatively short operating life of the pump—typically in the order of 5000 hours—is often one of the main factors limiting the reliability of a RGM. When the pump in a RGM fails, the sample gas flow may stop completely or decrease to an unacceptable level. In many RGMs, the sample flow is measured and an alarm is given to the user when the flow is too low. The value of such alarm is quite limited, however, because monitoring of respiratory gases is no more possible after a pump failure. In some RGMs, low flow may remain undetected and lead to measurement errors that may compromise patient safety.

In the prior art, the gas pump in a RGM is running always when the RGM is switched on. Alternatively, unnecessary operation of the pump can be prevented by manually setting the RGM to a "Standby" mode, when gas monitoring is not needed. When a patient is again connected to the RGM, the user must manually switch the monitor from the Standby mode to the normal Operation mode. Often the RGM is kept running continuously for long periods of time even if the need for gas monitoring would be only very intermittent. The reason for this is that many RGMs need warm up time of several minutes, and most users want to avoid waiting for the warm-up by keeping their RGMs continuously on. It is common that the RGM is switched on in the morning or at the beginning of a work shift and turned off in the evening or at the end of the work shift. In some hospitals, the RGMs may even be switched on for 24 hours a day. A substantial part of the operating hours of the gas pump often consists of periods, when there is no need for respiratory gas monitoring. Even if the RGM could be manually switched to Standby mode, users tend to forget it, because they are busy with more important tasks, when disconnecting a patient from the RGM. If a gas pump is running for 12 hours a day, it typically fails about twice in three years, which means that it is one of the main factors limiting the "mean time between failures" of a RGM.

The gas pump in a RGM is connected to both the pneumatics in the RGM and to the electronics circuitry. The replacement of a failed pump must be performed very skillfully in order to eliminate risks for new damages to the electronic circuits, such as those caused by electrostatic discharges and new faults in the pneumatics system, such as gas leakages. Thus, only a qualified service technician may change the pump. This means that the replacement is costly and it may take a substantial time to have the RGM repaired after a pump failure.

SUMMARY OF THE INVENTION

The purpose of the present invention is to eliminate unnecessary operation of the sample gas pump in a RGM. Another purpose of the invention is to improve the reliability of the RGM by avoiding unnecessary wear of the gas pump.

According to the first aspect of the invention, when a pressure sensor is pressure— connected to a gas sampling line and electrical-signal-connected to a processing unit: A minimum value and a maximum value in the signal forwarded by said pressure sensor, and representing a minimum pressure and a maximum pressure respectively inside said gas sampling line, are detected by said processing unit; a difference between said minimum value and said maximum value is calculated, and is compared with a predetermined threshold value in/to said processing unit; and if said calculated difference is: below said threshold value said pump is switched off by said processing unit, and over said threshold value said pump is switched on by said processing unit.

According to the second aspect of the invention, when at least one other patient monitor device capable to detect values of at least one physiological signal from said patient, said other patient monitor is detection-connected to said patient and electrical-signal-connected to said processing unit: A minimum value and a maximum value of said one physiological signal are detected by said other patient monitor; a difference between said minimum value and said maximum value is calculated, and is compared with a predetermined threshold value in/to said processing unit; and if said calculated difference is: below said threshold value said pump is switched off by said processing unit, and over said threshold value said pump is switched on by said processing unit.

DETAILED DESCRIPTION OF THE PREFERRED EMBODIMENTS

Figure 3:
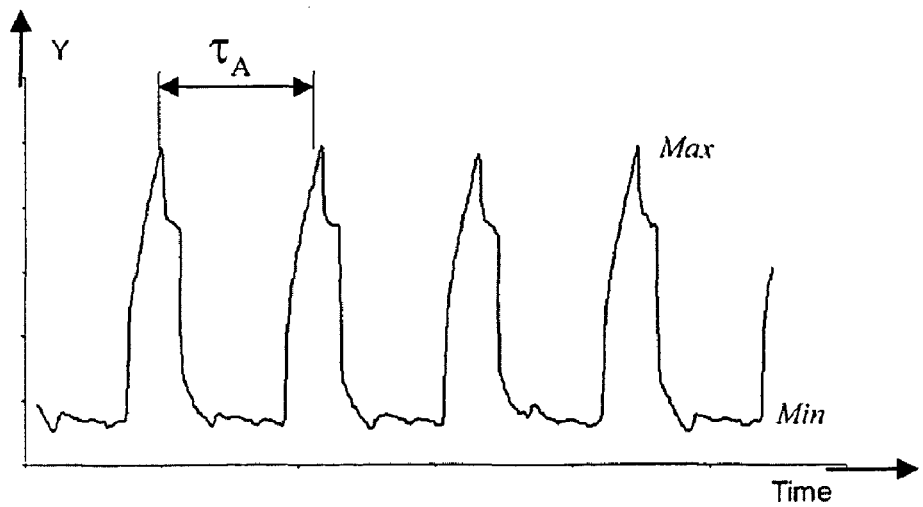
FIG. 3 shows an example of a typical respiratory signal, i.e. breathing air pressure or breathing airflow variations of a patient, which can be attained by e.g. a photoplethysmographic measuring unit. The exact form of the pulses can vary depending on the apparatus used for attaining the signal, but there are always the periodically repeated signal maxima and minima to be utilized by the invention.
Figure 4:
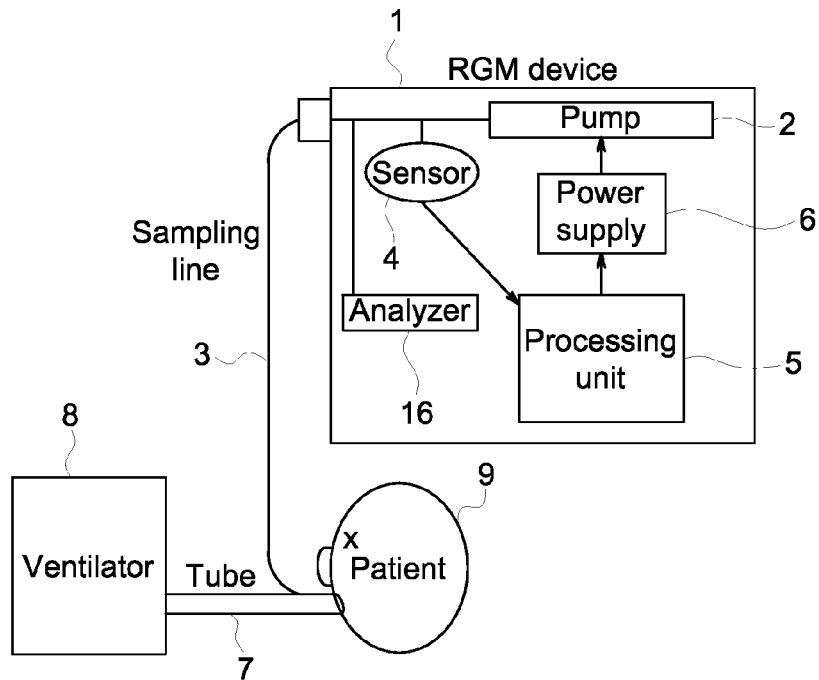
FIG. 4 shows schematically the first embodiment of the invention, in which the pressure sensor inherently present in the respiratory gas monitor device is utilized for detection of the presence/absence of a patient, and hence for switching on/off the gas pump in the respiratory gas monitor device.
Figure 5:
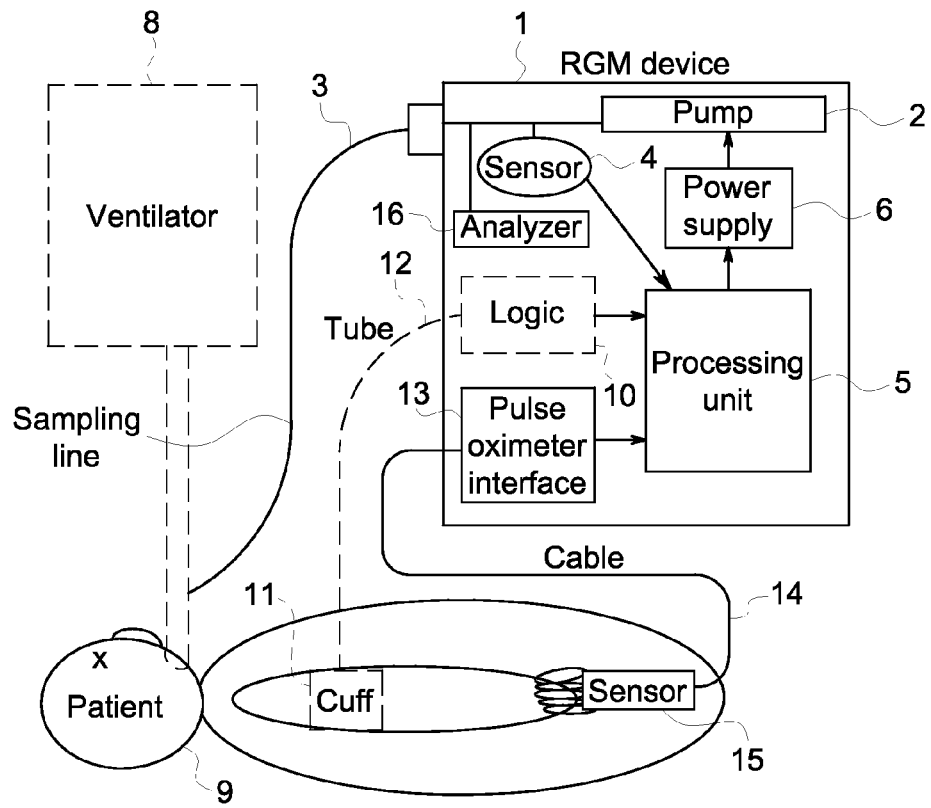
FIG. 5 shows schematically the second and the third embodiment of the invention, in which one other patient monitor device—in this case either a pulse oximeter, visualized by continuous lines, or a blood pressure cuff, visualized by broken lines—in most cases present for monitoring patient is utilized for detection of the presence/absence of a patient, and hence for switching on/off the gas pump in the respiratory gas monitor device. In the second embodiment there is a ventilator device and a breathing tube, and in the third embodiment there neither exists a ventilator device nor a breathing tube, but the gas sampling is made otherwise from the patient. The alternatives are visualized by dashed line of the ventilator device/breathing tube.
Figure 6:
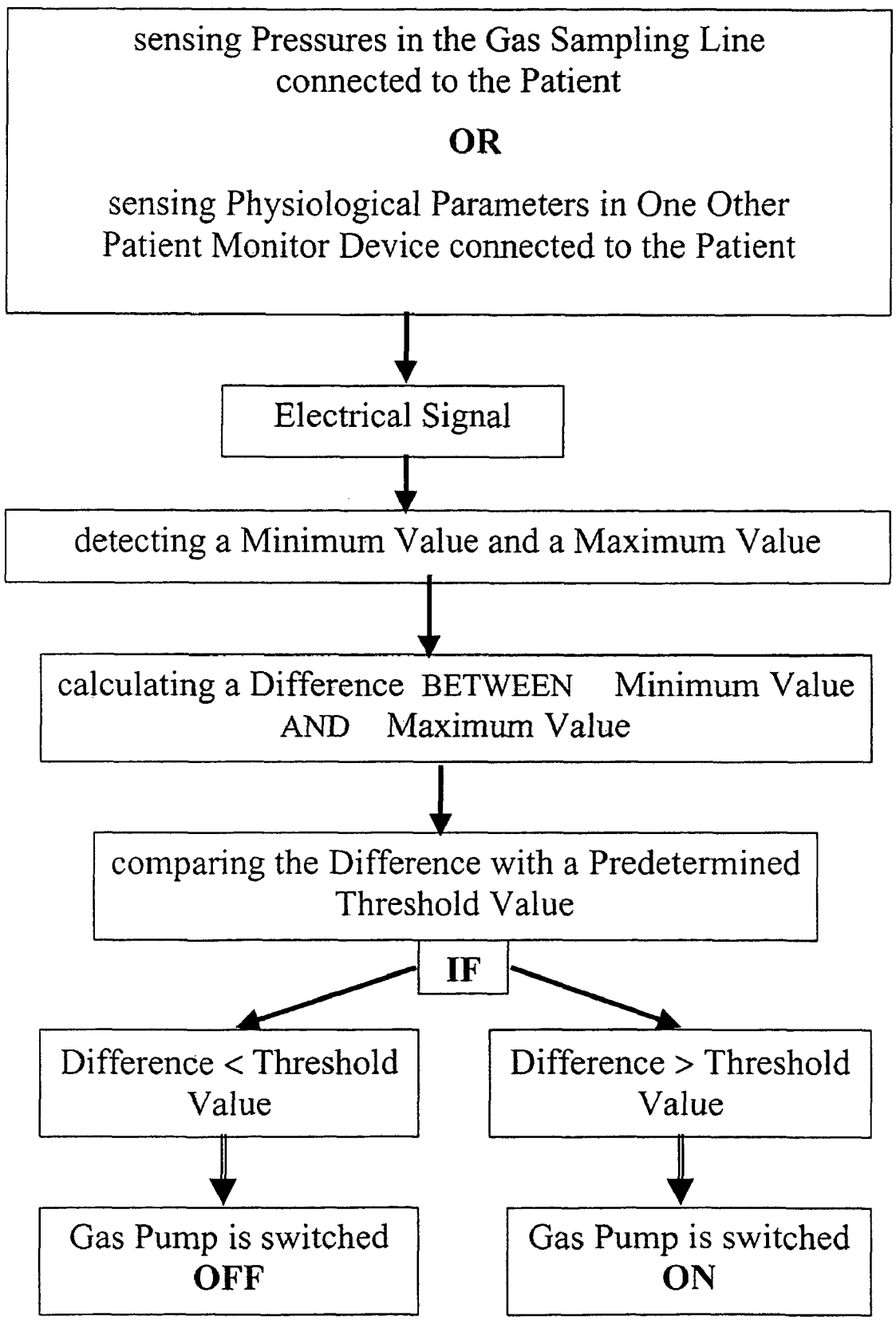
FIG. 6 shows the main steps of the method according to the invention.

The known respiratory gas monitor (=RGM) devices 1 comprise at least one respiratory gas analyzer 16 of a type applicable to analyze a gas component or gas components of the respiratory gas, i.e. gas components like $CO_2$ and/or oxygen and/or NO and/or $NO_2$ and/or $N_2O$ and/or other anesthetic gas component(s), which respiratory gas is fed to the patient and/or exhaled by the patient along a breathing tube 7. For this breathing purpose one end of the breathing tube 7 is connected to a ventilator device 8 and to the other end of the breathing tube 7 is connected to the patient 9. A gas sampling line 3 that is a thinner tube is flow-connected to the wider breathing tube 7. This gas sampling line 3 can be connected to the patient 9 also without the breathing tube 7 and the ventilator device 8. Accordingly, it is question about a diverting type or side flow monitoring of a patient. Because the respiratory gas analyzer 16 and the ventilator device 8 can be of any type appropriate for the purpose and known as such, they are not explained more in detail here. The respiratory gas monitor devices 1 further comprise a gas pump 2 for sucking sample of the respiratory gas from the breathing tube 7 through the gas sampling line 3, as well as a power supple 6 for providing electrical voltage/current to the gas pump 2, and a processing unit 5 for controlling this voltage/current to the gas pump, whereupon the gas pump creates a proper sample flow of the respiratory gas from the breathing tube to the respiratory gas analyzer 16. The respiratory gas monitor device 1 also comprises a pressure sensor 4, which is pressure-connected to the gas sampling line 3 and electrical-signal-connected to the processing unit 5. This electrical signal is normally used for correcting the measuring results of respiratory gas analyzer 16. As known, all pressure sensors 4 independent of their type have parts responsive to pressure and/or pressure variations, on the basis of which the sensors provide an electrical signal proportional to the pressure or pressure changes. Of course the proportionality not necessarily mean linear dependence, but proportionality can also be non-linear. FIG. 3 shows typical air pressure and/or airflow variations of breathing as measured by the pressure sensor 4. Processing unit 5 is typically a data processor together with necessary memories and other components. Processing unit can be a computer, but this is not necessary, because a more specialized design is in many cases more practical. Such processing units are widely used in various technical fields, and accordingly, they are not explained more in detail here.

Figure 1:
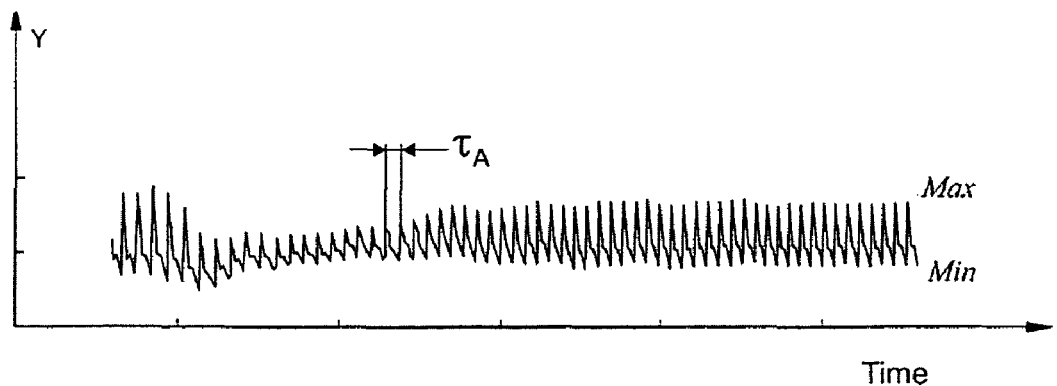
FIG. 1 shows an example of a typical cardiovascular pulse wave signal, i.e. blood pressure or blood flow variations of a patient, which can be attained by e.g. a photoplethysmography. The exact form of the pulses can vary depending on the apparatus used for attaining the signal, but there are always the periodically repeated signal maxima and minima to be utilized by the invention.
Figure 2:
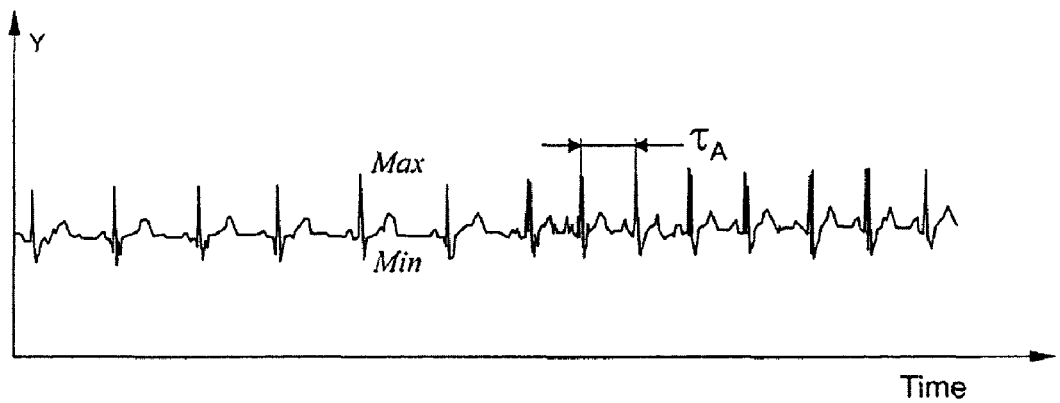
FIG. 2 shows an example of a typical electrocardiac or magnetocardiac signal representing cardiac excitation of a patient, which can be attained by an ECG- or a MCG-apparatus. The exact form of the pulses can vary depending on the positioning of the leads for attaining the signal, but there are always the periodically repeated signal maxima and minima to be utilized by the invention.

In most cases there is also some other patient monitor devices, and very often several other patient monitor devices, which is/are connected to the patient 9 under surgical operation or under medical control or the like, and which monitor device(s) is/are capable to detect values of at least one physiological signal from the patient 9. For this purpose the other patient monitor device(s) 10-12, 13-15 is/are detection-connected to said patient and electrical-signal-connected to the processing unit 5. One of the most usual of these other patient monitor devices is a Pulse Oximeter Device, which is the most usual of the photoplethysmographic devices, and which comprises at least a pulse oximeter sensor 15 that is connected with a pulse oximeter cable 14 and via a pulse oximeter interface 13 to the processing unit 5. As known, pulse oximeter sensors measure the blood amount in tissues of the patient—the tissue is typically a finger, but can also be an auricle, or any other part of the body—utilizing the transmittance or reflectance of an infrared radiation, whereupon a photoplethysmographic signal is received for further analysis. PhotoPlethysmoGraphy (=PPG) is known as such and is, accordingly, not explained more in detail here. Any kind of the photoplethysmographic devices can provide that kind of signal, which is useful for the invention. FIG. 2 shows typical blood flow/pressure variations as measured by the pulse oximeter device 13-15. One other of the usual of these other patient monitor devices is a Non Invasive Blood Pressure (=NIBP) measuring apparatus, which comprises a NIBP cuff 11 e.g. around an arm or some other respective body part, which cuff 11 is automatically pressurized and de-pressurized via a NIBP connection tube 12 for sensing the systolic and the diastolic blood pressures in the NIBP logics 10. The cuff 11 and the logics 10 together can be considered to be a blood pressure sensor. The systolic and the diastolic blood pressures are then forwarded to the processing unit 5. NIBP-apparatus does not reveal the temporal variability of the blood pressure or flow, but gives a mean value integrated over a time period, which respect the pressurizing and de-pressurizing time, as a result. This is one reason why the figures do not show any curve concerning NIBP measuring results. Still one other of the usual of these other patient monitor devices is an ElectroCardioGraphic (=ECG) device or MagnetoCardio-Graphic (=MCG) device, not shown in the figures, which comprise leads connected to the patient according to predetermined known lay-out. The ECG-device or MCG-device is also electrical-signal-connected to the processing unit 5. FIG. 1 shows typical variations in the cardiac excitation signal as measured by an ECG-device or a MCG-device.

According to the preferred embodiment of the present invention, the connection of a patient 1 to a RGM monitor 1 is automatically identified from the electric signal obtained from the pressure sensor 4 that measures the working pressure in the gas sampling line 3. Because of numerous effects of gas pressure on concentration measurements in the breathing air, it is always necessary to measure the working pressure and take its value into account when calculating the gas concentrations displayed to the user. Thus, the method disclosed by this invention does not require any extra components or mechanical or pneumatic constructions to the RGM.

The working pressure of the gas sensors in the RGM varies with the barometric pressure that is related with both weather conditions and altitude of the location of the RGM. These changes are very slow and can be considered irrelevant from the point of view of this invention; they merely define the pressure baseline. When a patient is connected to the anesthesia machine or ventilator and is not breathing spontaneously, pressure in the patient circuit varies cyclically in the pace of ventilation given to the patient. During the inspiration phase, there is an over pressure of 10-100 mbar. During the expiration phase the pressure drops when gas flows out of the patient's lung. The peak-to-peak amplitude of the pressure signal caused by the ventilation of the patient is between 10 and 100 mbar and the frequency of the cyclic pressure waveform equals that of the Respiration Rate of the ventilation. The exact waveform of the cyclic pressure variation depends on the settings of the ventilator and properties of the patients' airway and lung. When the gas pump in an RGM is not operating, there is no gas flow in the sampling line and accordingly no pressure drop that could change because of changes in the flow resistance of the sampling line. When the sample pump is running, the pressure drop across the sampling line may vary, if the flow resistance of the sampling line varies, for example when water vapor from the sample gas is condensing in the sampling line.

Due to the pressure conditions described above, the working pressure of the RGM remains on the baseline level when there is no patient connected to the RGM. When a patient is connected to the RGM, the working pressure changes in the pace $\tau_A$ of ventilation of the patient. According to the present invention, the need for respiratory gas monitoring is identified from the variations in the working pressure: when the working pressure stays constant, there is no need for gas monitoring and whereas cyclic changes in the working pressure indicate that gas monitoring is needed and the sample pump must be turned on.

The above-mentioned automatic identification is accomplished by analyzing the pressure signal from the pressure sensor 4 in the processing unit 5. The minimum values and maximum values of the working pressure is detected from the received pressure signal within a predetermined period of time, called hereafter the "Recording Period" RP, and comparing the difference between the maximum and minimum values to a threshold value, called hereafter the "Monitoring Threshold" MT. The values are of course stored in memories/memory in the processing unit 5 for further calculation purposes. If there is no patient connected to the RGM, the working pressure is essentially constant and the difference between its maximum and minimum values within the RP will be below the MT. In this case, the gas pump may stay off or can be switched off in order to keep the RGM in the Standby mode or switch it to that mode. If the gas sampling line is connected to the airway of a patient to be monitored, the working pressure will vary at the pace $\tau_A$ Of respiration and the difference between maximum and minimum pressures during the RP will exceed the MT. In this case, the gas pump must stay on or be switched on in order to keep the RGM in its normal operating mode or automatically switch it to that mode.

Accordingly, a minimum value Min and a maximum value Max in the signal Y forwarded by the pressure sensor 4 to the processing unit 5 are detected by the processing unit 5, which minimum value Min and maximum value Max represent the minimum pressure(s) and the maximum pressure(s) respectively inside said gas sampling line 3. When the signal Y is periodically variable because of intrinsic physiological reasons—i.e. pulsing or alternating or between these like blood flow signal from PPG—a mean minimum value Min and a mean maximum value Max is calculated over the recording period RP. In this kind of cases—signal variable because of intrinsic physiological reasons—the recording period RP is several times the pace of the pulses, typically $RP > 10 \times \tau_A$. Accordingly, differences between single pulses are eliminated. Next a difference Max−Min between the minimum value and the maximum value is calculated, and is compared with a predetermined threshold value MT in said processing unit 5. If the calculated difference is below the threshold value, i.e. Max−Min<MT, the pump 2 is switched off or kept in the prevailing non-operating state by the processing unit 5 utilizing e.g. the power source 6. Alternatively, if the calculated difference is over the threshold value, i.e. Max−Min>MT, the pump 2 is switched on or kept in the prevailing operating state by the processing unit 5 utilizing e.g. the power source 6.

The need for respiratory gas monitoring can be identified separately for successive recording periods RP, which can be consecutively separate, i.e. follow each other as separate periods, or have temporal overlap, i.e. can have some common pulses, whereupon the periods can also have a moving time window as the RP. In this case, the most recent data points representing the working pressure are included to the calculations for maxima and minima of the working pressure and the oldest data points are simultaneously dropped out from these calculations. The recording periods RP for turning the gas pump off $RP_{OFF}$ and on $RP_{ON}$ can differ in their durations. In order not to turn the gas pump off too quickly, the $RP_{OFF}$ can be 2-5 minutes. In order to turn the gas pump on soon enough after the connection of a patient to the RGM, the $RP_{ON}$ can be 5-50 seconds.

In many cases, an RGM has the capability to monitor other one or more physiological signals in addition to respiratory signals. In order to monitor these other signals, sensors or electrodes generating or capturing the corresponding physiological signals are connected to such an RGM. These signals can for example originate from a Pulse Oximetry sensor for monitoring the Oxygen saturation of blood often called as $SpO_2$, blood pressure sensor for Blood Pressure Monitoring called as BP or electrodes for ElectroCardioGraphic Monitoring called ECG or MagnetoCardiaGraphic Monitoring called MCG. The need for respiratory monitoring can be detected from one or more of the physiological signals mentioned above. The detection can be done registering the minimum and maximum values as described next.

According to two further embodiments of the invention the connection of a patient 1 to a RGM monitor 1 is automatically identified from the electric signal Y obtained either from the pulse oximeter sensor 15—or some other sensor working according to an analogous principle—that measures the blood flow in the tissue of the patient 9 providing e.g. a PPG-signal, or from ECG-device or MCG-device that measures the cardiac excitation from the patient 9 providing a physiological electrical/magnetic signal Y. In these cases the signals are attained by different means from the body of the patient 9, but all of them somehow describe the working of patient's heart, and accordingly these signals are called with a common name "Heart Signal". The same procedure as in measuring pressures of the breathing air, described above, is also valid for these latter cases, where heart signal is received and used, i.e. only slow changes need to be taken account, and the variations at the paces $\tau_A$ of heart pulses are omitted. ECG and MCG are considered to be sensors, too. The above-mentioned automatic identification is accomplished by analyzing the heart signal from the Pulse Oximeter or ECG-device or MCG-device in the processing unit 5. The minimum values and maximum values of the heart signal Y is detected within a predetermined recording period RP, and comparing the difference between the maximum and minimum values to a threshold value MT. Accordingly, a minimum value Min and a maximum value Max in the signal Y forwarded by the sensor to the processing unit 5 are detected by the processing unit 5, which minimum value Min and maximum value Max represent the minimum blood flow(s) or minimum cardiac excitation(s) and the maximum blood flow(s) or maximum cardiac excitation(s) respectively in the patient. This signal being periodically variable because of intrinsic physiological reasons—i.e. pulsing or alternating or between these like blood flow signal Y from PPG—a mean minimum value Min and a mean maximum value Max is calculated over the recording period RP. Here too, the recording period RP is several times the pace of the pulses, typically RP>10×$\tau_A$. Accordingly, differences between single pulses are eliminated. Next a difference Max−Min between the minimum value and the maximum value is calculated, and is compared with a predetermined threshold value MT in said processing unit 5. If the calculated difference is below the threshold value, i.e. Max−Min<MT, the pump 2 is switched off or kept in the prevailing non-operating state by the processing unit 5 utilizing e.g. the power source 6. Alternatively, if the calculated difference is over the threshold value, i.e. Max−Min>MT, the pump 2 is switched on or kept in the prevailing operating state by the processing unit 5 utilizing e.g. the power source 6.

According to still one further embodiment of the invention the connection of a patient 1 to a RGM monitor 1 is automatically identified from the blood pressure signal from non-invasive blood pressure (=NIBP) measuring apparatus 10-12, which through pressurizing and de-pressurizing of the cuff aided by detection of pulse stopping and restarting provides the systolic and the diastolic blood pressure signal. The attained systolic blood pressure value is directly the mean maximum value Max of the signal and the attained diastolic blood pressure value is directly the mean minimum value Min of the signal, which are either already in or forwarded to the processing unit 5. Here the pressurizing and de-pressurizing times together form the predetermined recording period RP. From this point onwards the rest of the steps are same as performed in the other embodiments. Accordingly, a difference Max−Min between the minimum value and the maximum value is calculated, and is compared with a predetermined threshold value MT in said processing unit 5. If the calculated difference is below the threshold value, i.e. Max−Min<MT, the pump 2 is switched off or kept in the prevailing non-operating state by the processing unit 5 utilizing e.g. the power source 6. Alternatively, if the calculated difference is over the threshold value, i.e. Max−Min>MT, the pump 2 is switched on or kept in the prevailing operating state by the processing unit 5 utilizing e.g. the power source 6.

To avoid errors caused by self-generated noise and by electrical and magnetic fields in the environment and/or by possible other disturbances from outside the respiratory gas monitor device and/or the mentioned at least one other patient monitor device capable to detect values of at least one physiological signal from said patient, which erroneous/disturbing "signal" may be fed into the RGM 1 through pressure sensor 4, through pulse oximeter sensor 15, through ECG-device or MCG-device and/or through NIBP measuring apparatus 10-12 especially when the devices are not connected to the patient, i.e. during instances when there is no patient and the pump should be switched off, the actual signal—in fact everything that could be an input from the above mentioned sensors to the processing unit 5—is low-pass filtered before the detection of the minimum value Min and the maximum value Max. This kind of simple filtering is in most cases very effective, because noise and other disturbances have normally high frequency compared to the frequencies of the genuine signal from the sensors 4, 15, 10-11, ECG, MCG. Heart rate is in most cases at maximum about 200 pulses/minute, and breathing rate is in most cases at maximum about 100 respirations/minute, while disturbances normally have a frequency of at least 50 Hz or 60 Hz, and mainly in the order of radio frequencies. Accordingly, low-pass filtering with a cut-off frequency at maximum 10 Hz, or in the order of 5 Hz is practical and efficient.

The detection of the presence of a patient connected to the RGM can also rely on the parameter specific algorithms that derive numeric values or waveforms for a physiological parameter from the corresponding physiological signals: A patient is considered to be connected to the RGM, if a value or values or waveform for at least one physiological signal is shown on the monitor's display or is in a state enabling a detection or visualization of the value(s) or waveform, whereupon possible noise signal components or error signal components are filtered away from the raw signal available from the signal detector(s) resulting to a clean duty or utility signal. This means that if a $SpO_2$-monitor, a BP-monitor, an ECG-monitor or a MCG monitor gives a data or can give a data the mentioned minimum values and maximum values can be derived from this data. Normally all monitors detecting and analyzing physiological signal(s) from a patient are provided with means that include algorithm(s) to remove erroneous signal components, i.e. there is ECG-algorithm, $SpO_2$-algorithm etc. to filter noise and respective signal components away from the raw signal. Some monitors have so called LEADS OFF-alarm, in which case: 1} IF "LEADS OFF"-alarm is activated or ON no electrical-signal is forwarded to the processing unit, whereupon no difference between a non-existing minimum value and a non-existing maximum value is available→meaning non-presence of a patient, or 2} IF "LEADS OFF"-alarm is not activated or OFF an electrical-signal—a duty or utility signal—is forwarded to the processing unit, whereupon a difference between an existing minimum value and an existing maximum value is available→meaning presence of a patient.

Even if the RGM would only be capable of monitoring respiratory signals, it may be a part of a monitoring system that is used for monitoring both respiratory and other physiological signals. In this case, the presence of a patient connected to the monitoring system can be communicated to the RGM by at least one of the other monitors belonging to the monitoring system whenever it detects the patient or the user commands it to start the patient monitoring.

In all these cases, the potential need of the gas monitoring is identified from the behavior of the signals from sensors that are used for patient monitoring. Many RGMs or combinations of a RGM with other patient monitoring devices contain a number sensors and devices, which measure various physiological signals. The presence of a patient to be monitored can be identified from almost any of the parameter signals obtained this way, or combinations of the parameter signals.

For the purpose of the invention oxygen saturation of blood, blood pressure, blood flow, electrical heart signal, magnetic heart signal, electrical muscular signal and electrical brain signal etc. can be used. It shall be noted that the respiratory gas analyzer and the other patient monitor device can be in one unit or separate units.

The invention claimed is:

1. A method for controlling a respiratory gas monitor device, the respiratory gas monitor device including:
   at least one respiratory gas analyzer,
   a gas sampling line flow-connected to a breathing tube suitable for feeding of respiratory gas to and from a patient,
   a gas pump for sucking sample(s) of respiratory gas from said breathing tube through said gas sampling line, a power supply and a processing unit, and a pressure sensor pressure-connected to said gas sampling line and electrical-signal-connected to said processing unit, wherein the method comprises:

detecting by said processing unit a minimum value and a maximum value in the signal forwarded by said pressure sensor, wherein the minimum value in the signal represents a minimum pressure and wherein the maximum value in the signal represents a maximum pressure respectively inside said gas sampling line;

calculating a difference between said minimum value and said maximum value;

comparing said calculated difference with a predetermined threshold value programmed in or to said processing unit; and (a) if said calculated difference is below said threshold value, switching said gas pump off or keeping said gas pump non-operating by said processing unit, and (b) if said calculated difference is over said threshold value, switching said gas pump on or keeping said gas pump operating by said processing unit.

2. The method of claim 1, wherein said minimum value and said maximum value are detected within a predetermined recording period.

3. The method of claim 2, wherein said recording period is predetermined to be a longer recording period for turning the gas pump off, and a shorter recording period for turning the gas pump on.

4. The method of claim 3, wherein said longer recording period for turning the gas pump off is from 2 to 5 minutes.

5. The method of claim 3, wherein said shorter recording period for turning the gas pump on is from 5 to 50 seconds.

6. The method of claim 2 having a plurality of said recording periods following each other in succession.

7. The method of claim 6, wherein said successive recording periods are arranged to be: periods consecutively separate; or periods having temporal overlap.

8. The method of claim 1, wherein said signal forwarded by said pressure sensor is low-pass filtered before said detection of the minimum value and the maximum value.

9. A method for controlling a respiratory gas monitor device in a patient monitoring system, the respiratory gas monitor device including:

at least one respiratory gas analyzer, a gas sampling line flow-connected to the patient, a gas pump for sucking sample(s) of respiratory gas from the patient through said gas sampling line to said respiratory gas analyzer, and a power supply and a processing unit; and at least one other patient monitor device capable to detect values of at least one physiological signal from said patient, said other patient monitor detection-connected to said patient and electrical-signal-connected to said processing unit;

wherein the method comprises:

detecting by said other patient monitor a minimum value and a maximum value of said one physiological signal;

calculating a difference between said minimum value and said maximum value;

comparing said calculated difference with a predetermined threshold value programmed in or to said processing unit; and (a) if said calculated difference is below said threshold value, switching said gas pump off or keeping said gas pump non-operating by said processing unit, and (b) if said calculated difference is over said threshold value, switching said gas pump on or keeping said gas pump operating by said processing unit.

10. The method of claim 9, wherein said other patient monitor device detects a physiological signal selected from a group of signals including at least oxygen saturation of blood, blood pressure, blood flow, electrical heart signal, magnetic heart signal, electrical muscular signal and electrical brain signal.

11. The method of claim 9, wherein said minimum value and said maximum value are detected within a predetermined recording period.

12. The method of claim 11, wherein said recording period is predetermined to be a longer recording period for turning the gas pump off, and a shorter recording period for turning the gas pump on.

13. The method of claim 12, wherein said longer recording period for turning the gas pump off is from 2 to 5 minutes.

14. The method of claim 12, wherein said shorter recording period for turning the gas pump on is from 5 to 50 seconds.

15. The method of claim 11 having a plurality of said recording periods following each other in succession.

16. The method of claim 15, wherein said successive recording periods are arranged to be: periods consecutively separate; or periods having temporal overlap.

17. The method of claim 9, wherein said signal forwarded by said one other patient monitor device is low-pass filtered before said detection of the minimum value and the maximum value.

18. The method of claim 9, wherein said patient is free breathing or breathing via a breathing tube.

19. The method of claim 9, wherein said respiratory gas analyzer and said at least one other patient monitor device are a single unit or separate units.

* * * * *